US008372425B2

(12) United States Patent
Loftsson et al.

(10) Patent No.: US 8,372,425 B2
(45) Date of Patent: Feb. 12, 2013

(54) FATTY ACIDS FOR USE AS A MEDICAMENT

(75) Inventors: Thorsteinn Loftsson, Reykjavik (IS);
Einar Stefansson, Reykjavik (IS)

(73) Assignee: Lipid Pharmaceuticals EHF. (IS)

( * ) Notice: Subject to any disclaimer, the term of this patent is extended or adjusted under 35 U.S.C. 154(b) by 526 days.

(21) Appl. No.: 12/609,845

(22) Filed: Oct. 30, 2009

(65) Prior Publication Data
US 2010/0113387 A1  May 6, 2010

Related U.S. Application Data

(60) Provisional application No. 61/174,144, filed on Apr. 30, 2009, provisional application No. 61/110,093, filed on Oct. 31, 2008.

(51) Int. Cl.
*A61K 35/60* (2006.01)
*A61K 9/02* (2006.01)

(52) U.S. Cl. .................. 424/436; 424/554; 424/522

(58) Field of Classification Search .................. None
See application file for complete search history.

(56) References Cited

U.S. PATENT DOCUMENTS

| 4,657,900 | A | 4/1987 | Powell et al. | |
|---|---|---|---|---|
| 5,039,703 | A | 8/1991 | Breuer | |
| 6,193,993 | B1 * | 2/2001 | Murahashi et al. | 424/436 |
| 6,391,869 | B1 | 5/2002 | Parks et al. | |
| 6,414,016 | B1 * | 7/2002 | Ueno | 514/456 |
| 6,596,767 | B2 | 7/2003 | Masor et al. | |
| 6,964,786 | B1 | 11/2005 | Khanna | |
| 7,491,522 | B2 | 2/2009 | Haraldsson et al. | |
| 7,722,906 | B2 | 5/2010 | Kandil | |
| 7,893,106 | B2 | 2/2011 | Arterburn et al. | |
| 2008/0011441 | A1 | 1/2008 | Oswald et al. | |
| 2008/0193406 | A1 * | 8/2008 | Rull Prous et al. | 424/78.03 |
| 2009/0247494 | A1 | 10/2009 | Kofsky | |

FOREIGN PATENT DOCUMENTS

| AU | 2009202036 A1 | 6/2009 |
|---|---|---|
| EP | 420056 A2 | 9/1990 |
| EP | 1022019 A1 | 7/2000 |
| WO | 95/24459 A1 | 9/1995 |
| WO | 9735570 | 10/1997 |
| WO | 00/44862 A1 | 8/2000 |
| WO | 00/49117 A1 | 8/2000 |
| WO | 2006132968 A1 | 12/2006 |
| WO | 2007046122 A2 | 4/2007 |
| WO | 2007076531 A1 | 7/2007 |
| WO | 2008056389 A1 | 5/2008 |

OTHER PUBLICATIONS

Burdock (Toxicology and pharmacology of sodium ricinoleate, 44 Food and Chem. Toxicology 1689 (2006).*
B.E. Lacy and L.C. Levy, Lubiprostone: a novel treatment for chronic constipation, Clin. Interv. Aging 3, 357-364, 2008.
C. Vieira et al., Effect of ricinoleic acid in acute and subcronic experimental models of inflammation, Med. Inflammation, 9, 223-228, 2000.
G.A. Burdock et al., Toxicology and pharmacology of sodium ricinoleate, Food Chem. Tox., 44, 1689-1698, 2006.
H. Thormar et al., The role of microbicidal lipids in host defense against pathogens and their potential as therapeutic agents, Chem. Phys. Lip., 150, 1-11, 2007.
Halldorsson et al., Lipase selectivity towards Fatty Acids Commonly Found in Fish Oil,. Eur. J. Lipid Sci. Tech. 106, 79-87, 2004, Abstract, 2 pages.
J.J. Kabara, Fatty acids and derivatives as antimicrobial agents. In: The pharmological effect of lipids. Edited by J.J. Kabara. The American Oil Chemists Society, St. Louis, MO, 1978, pp. 1-13.
N.M. Carballeira, New Advances in fatty acids as antimalarial, antimycobaterial and antifungal agents, Prog. Lipid Res., 47, 50-61, 2008.
Osman et al., Monoglycerides: I. Synthesis by Direct Esterification of Fatty Acids and Glycerol, Fette, Seifen Anstrichmittel, 70, 331-333, 2006, Abstract, 1 page.
S. Khulushi et al., The effect of unsaturated fatty acids on *Heliobacter pylori* in vitro, J. Med. Microbiol. 42, 276-282,1995, Abstract, 2 pages.
Kabara et al., Antimicrobial Agents Derived from Fatty Acids, JAOCS, vol. 61, No. 2, Feb. 1984, pp. 397-403.
CN1679838 A, Abstract, Oct. 12, 2005.
CN1686230 A, Abstract, Oct. 26, 2005.
CN1709337 A, Abstract, Dec. 21, 2005.
DE3739700 A1, Abstract, Jun. 8, 1989.
DE4022815 A1, Abstract, Jan. 23, 1992.
KR20010001512 A, Abstract, Jan. 5, 2001.
PCT/IS2009/000012 International Search Report and Written Opinion, date of mailing Feb. 1, 2010, 20 pages.

* cited by examiner

*Primary Examiner* — Robert A Wax
*Assistant Examiner* — Sarah Park
(74) *Attorney, Agent, or Firm* — Cantor Colburn LLP

(57) ABSTRACT

The invention relates to fatty acid stimulation of rectal mucosa initiating the process of defecation, acting as a laxative. Furthermore, the invention relates to the usage of free fatty acids, fatty acid mixtures and fatty acid extracts from marine lipids in pharmaceutical formulations such as suppositories, ointments, tablets and gelatin capsules for treatment and prevention of multiple disorders like constipation, hemorrhoids, bacterial infections (e.g. *helicobacter pylori*), viral infections (e.g. herpes simplex virus infections) and inflammations, as well as against fissura ani and pruritus ani.

10 Claims, No Drawings

FATTY ACIDS FOR USE AS A MEDICAMENT

TECHNICAL BACKGROUND AND PRIOR ART

Laxatives are used to treat constipation, i.e. the absence of regular defecation, accumulation of feces in the colon and/or the passage of small amounts of hard, dry stools. People who are constipated may find it difficult and painful to have a bowel movement. Laxatives are also used to cleanse the lower bowel before a proctoscopy, rectoscopy, colonoscopy, x-ray imaging of the colon or similar diagnostic procedure. There are several types of laxatives, see overview in Table 1. Laxatives can produce side effects, but usually not serious ones. Stimulants and irritants are more likely than other types of laxatives to cause side effects such as abdominal discomfort, faintness and cramps. Laxatives may be for oral administration, e.g. tablets, capsules and liquids, or for rectal administration, e.g. suppositories and enemas. Orally administered laxatives can reduce bioavailability of drugs and nutrients.

Castor oil is a well known laxative, a usual therapeutic adult dose for laxative effect is 15 to 60 mL, administered orally. About 90% of the fatty acid content in castor oil is the triglyceride formed from ricinoleic acid (12-hydroxy-9-cis-octadecenoic acid), a monounsaturated fatty acid, which is the active component of castor oil, acts as a laxative by stimulating secretion of fluid and electrolytes in the small intestines. One or two copious of semi-fluid stools are released within 2 to 6 hours of the administration. Ricinoleic acid is effective in preventing the growth of numerous species of viruses, bacteria, yeasts and molds, and it does possess some anti-inflammatory effect (Vieira et al. 2000; Burdock et al. 2006). Short chain fatty acids, such as lactic, acetic, butyric and propionic acid, can stimulate colonic motility and by increasing the osmotic pressure (i.e. hyperosmotic agents, Table 1).

Lubiprostone (difluoropentyl-2-hydroxy-6-oxooctahydrocyclopenta-heptanoic acid) is a bicyclic fatty acid derived from a metabolite of prostaglandin E1. After oral administration lubiprostone activates specific chloride channels (C1C-2 channels) in the gastro-intestinal tract to stimulate intestinal fluid secretion, increase GI transit, and improve symptoms of constipation (B. E. Lacy 2008). Thus, lubiprostone has a receptor specific effect.

TABLE 1

Types of laxatives

| Class | Site of action | Onset of action | Mechanism of action | Examples |
|---|---|---|---|---|
| Bulk-producing agents | Small and large intestine | 12-72 hours | Increase the volume of the stool (retain more water), and will both soften the stool and stimulate intestinal motility. | Psyllium, methylcellulose, dietary fibers |
| Stool softeners and surfactants | Small and large intestine | 12-72 hours | Hold water and fats within the stool, making it easier to move along. | Docusate (a surfactant) |
| Saline | Small and large intestine | 0.5-6 hours | Retain water in the intestinal lumen, increasing intraluminal pressure leading to softer stool. | Magnesium hydroxide, magnesium sulfate, sodium phosphate |
| Lubricants and emollients | Colon | 6-8 hours | Make the stool slippery so that it slides through the intestine more easily. Retards absorption of water. | Mineral oil |
| Hyperosmotic agents | Colon | 0.5-3 hours | Act by the osmotic effect that retains water within the intestine | Sorbitol, lactulose, polyethylene glycol, glycerin suppositories |
| Stimulants and irritants | Colon | 6-10 hours | Stimulate peristaltic action, i.e. contraction of smooth muscles that propel contents through the digestive tract. | Bisacodyl tablets, senna |
|  | Colon | 6-8 hours |  | Phenolphthalein |
|  | Small intestine | 2-6 hours |  | Castor oil |
|  | Colon | 0.25-1 hour |  | Bisacodyl suppositories |
| Foods |  |  |  | Figs, olive oil, prunes |

It has been documented that saturated and unsaturated fatty acids possess both antibacterial and antiviral activity, and that the fatty acids play a role in the natural defense against infections in mucosal membranes and skin, see e.g. Kabara (1978). In vitro studies have shown that free fatty acids kill enveloped viruses, such as Herpes simples-1 and Herpes simplex-2, Gram-positive bacteria, Gram-negative bacteria, such as *Helicobacter pylori*, and fungi (see Khulushi et al. (1995), Thormar et al. (2007), Carballeira (2008)).

The dietary and nutritional benefits of essential fatty acids are well known and dietary supplements such as fish oils have been used for a long time, providing poly-unsaturated fatty acids (PUFAs), also referred to as highly-unsaturated fatty acids (HUFAs), in the form of triacylglycerides (TAGs) also called triglycerides. The so called essential omega-3 fatty acids are particularly beneficial.

EP 420056 discusses that fat base suppositories, in particular those based on non-lauric cocoa butter substitute, can cause irritation which is induce by the fat base. The document suggests to add to the suppositories fatty acids, fatty acid salts or fatty acid esters to reduce the irritation caused by the fat base.

New laxatives with little side effects and discomfort would be much appreciated.

SUMMARY OF INVENTION

The invention is based on the surprising discovery that fatty acids have a clear and significant laxative effect and can be beneficially used to initiate defecation in subjects suffering from constipation and/or hard stools or where cleansing of the rectum and lower bowel. Examples provided herein demonstrate a clear and convincing effect of fatty acids in this regard. Pharmaceutical dosage forms are provided and medical methods based on these findings.

The gastrointestinal tract wall (rectal mucosa) contains polymodal nociceptors which are activated by a variety of mechanical, chemical, or osmotic stimuli and send via primary afferent neurons information to the enteric nervous system (intrinsic innervation) and to the CNS via sympathetic and parasympathetic pathways (extrinsic innervations). The inventors have discovered that free fatty acids and fatty acid mixtures act as chemical bowel stimulant on the polymodal nociceptors in the rectal mucosa initiating the process of defecation.

Pharmaceutical dosage forms for other medical conditions are also presented, based on the anti-inflammatory, antiviral and antibacterial effects of the fatty acids. Provided herein are dosage forms for treatment of diseases and conditions including hemorrhoids, fissura ani and pruritus ani. New and useful compositions of fatty acids are disclosed, including compositions with fatty acids and cyclodextrins, which are shown to be stable and effective.

Hemorrhoids, anal fissure and pruritus ani are all common benign anal diseases that conventionally rely on corticosteroid based medication for their treatment. The present invention substitutes steroid-containing drugs with non-steroid products derived from natural sources such as fish oil, in addition to the use of these products as laxatives.

DETAILED DESCRIPTION

The invention provides in a first aspect a pharmaceutical dosage form for administration to rectum and/or the large intestine for the purpose of inducing defecation (bowel movements), i.e. inducing and/or stimulating the process. The dosage form comprises as an active ingredient one or more fatty acid. The one or more fatty acid is suitably in a form selected from free fatty acid, salt of fatty acid with a pharmaceutically acceptable counter ion, fatty acid ethyl ester and fatty acid monoglyceride. Free fatty acids are the presently preferred embodiment.

The one or more fatty acid preferably has a chain length in the range of four to 36 carbon atoms, such as a chain length in the range of 4 to 24 and more preferably a chain length in the range of 8 to 24 carbons. More preferably the one or more fatty acid comprise a mixture of fatty acids, which can be derived from suitable natural lipid material such as oils of animal or vegetative origin, fractions thereof or a mixture thereof.

Fatty acids useful in the invention include saturated fatty acids such as hexanoic acid (caproic acid) (6:0), heptanoic acid (enanthic acid) (7:0), octanoic acid (caprylic acid) (8:0), nonanoic acid (pelargonic acid) (9:0), capric acid (10:0), undecylenic acid (11:0), lauric acid (12:0), tridecylic acid (13:0), myristic acid (14:0) palmitic acid (16:0), and stearic acid (18:0). Unsaturated fatty acids which are useful include palmitoleic acid (16:1 n-7), oleic acid (18:1 n-9), elaidic acid (18:1), linoleic acid (18:2 n-6), linolenic acid (18:3), arachidonic acid (20:4 n-6), gadoleic acid (20:1 n-11), gondoic acid (20:1 n-9; cis-11 eicosenoic acid), erucic acid (22:1 n-9) and cetoleic acid (22:1 n-11).

Useful vegetable oils as raw material for the fatty acids of the invention include safflower oil, corn oil, almond oil, sesame oil, soybean oil, linseed oil, rapeseed oil, grape seed oil, sunflower oil, wheat germ oil, hemp oil, and any mixtures thereof.

In preferred embodiments the fatty acids are derived from oil material which is pharmaceutically acceptable and defined according to Pharmacopoeia standards (pharmaceutical grade oils). Such oils include marine omega oils such as Omega-3 Fish Oil (Lysi, Iceland).

In a preferred embodiment the one or more fatty acids comprise a mixture of fatty acids comprising at least about 20 wt % of unsaturated fatty acids and at least about 5 wt % polyunsaturated fatty acids. The term poly-unsaturated fatty acid indicates a fatty acid with more than one double bond in its acyl sidechain and is used herein interchangeable with the term highly-unsaturated fatty acid or HUFA. Many natural oils provide such fatty acid composition, e.g. the vegetable oils mentioned above, and fish oils and other marine oils as well, which provide a high fraction of PUFA. Among polyunsaturated fatty acids useful in the invention are the omega-3 fatty acids alpha-linolenic acid (18:3), stearidonic acid (18:3), moroctic acid (18:4 n-3), eicosatrienoic acid (20:3), eicosatetraenoic acid (20:4), eicosapentaenoic acid (20:5; EPA), docosapentaenoic acid (22:5), docosapentaenoic acid (22:5), and docosahexaenoic acid (22:6; DHA), tetracosapentaenoic acid (24:5), and tetracosahexaenoic acid (24:6). Other useful polyunsaturated fatty acids are omega-6 fatty acids including linoleic acid (18:2 n-6), gamma-linolenic acid (18:3 n-6), eicosadienoic acid (20:2). The designation in parantheses indicates the total number of carbon atoms in the acyl chain and the number of double bonds, thus 18:3 is a fatty acid with 18 carbon atoms and three double bonds. The omega number indicates how far from the lipophilic end of the acyl chain the first double bond is situated, also indicated with n, as is used for other unsaturated fatty acids above.

In a useful embodiment, the pharmaceutical dosage form comprises a mixture of fatty acids derived from marine organisms. Marine organisms useful as sources of the fatty acid material include marine animal oil derived from an animal source selected from fish liver oil including cod liver oil, tuna oil; fish flesh or fish meal including flesh or meal from herring, capelin, mackerel, menhaden, sardine, anchovy, horse mackerel, blue whiting, and tuna; planktonic organisms, squid and molluscs.

Oils such as the above mentioned are readily converted to free fatty acids by hrolysis As mentioned above, the pharmaceutical dosage form of the invention for laxative action is suitably formulated for administration to rectum and/or lower intestines. Consequently, any type of dosage form suitable for administration at said site is within the scope of the present invention. Currently contemplated dosage forms include suppositories, ointment, cream, lotion, paste, gel, and formulations for enema delivery. Suppositories are well known in the art, they are generally formulated to be solid at room temperature and up to at least about 30° C. but having a melting temperature below the normal human body temperature of 37° C. It is therefore common to formulate suppositories with a fat base, such as cocoa butter, which fulfils the above melting point criteria. Cocoa butter is a mixture of triglycerides of saturated and unsaturated fatty acids which can be manipulated in solid form at room temperature but melts completely at body temperature. More recent materials include so called cocoa butter substitutes (CBS), which include the following categories: interesterified fully hydrogenated palm kernel oil, fully hydrogenated palm kernel stearine, mid fractions of hydrogenated vegetable oils which are rich in trans-fatty acids and semi-synthetic glycerides.

Useful commercially available fat bases suitable for the present invention include Suppocire™ (Gattefosse) lipophilic bases, a semi-synthetic vegetable based oil base available in several grades including Suppocire™ AS, AS2X, NA, Novata™ (Henkel Int.) including Novata A, Novata B, and Novata BC, Witepsol™ (Dynamit Nobel Ab) such as Witepsol™ H5, H12, H15, H32, H35, W25, W31, W32, W32, W35, and W45; Massa Estarinum™ (SASOL), incl. Massa Estarinum™ of the grades B, BC, E and 299.

The suppositories of the present invention may suitably comprise any of the above mentioned materials as base. Hydrophilic waxes can also be used in the invention, such as the polyethylene glycols (eg PEG 1500, PEG 3000, PEG 4000 and mixtures thereof). Suppocire AP, is an amphiphilic base comprising saturated polyglycolysed glycerides.

Further base components may suitably be added, such as beeswax, carnuba wax or the like.

The suppository dosage form may also in some embodiments comprise further excipients such as but not limited to binders and adhesives, lubricants, disintegrants, colorants and bulking agents.

Suppository dosage forms of the invention will generally comprise in the range of 50-2000 mg of the fatty acid active ingredient, and preferably in the range of 50-1000 mg, such as in the range of 100-750 mg, including about 100 mg, about 200 mg, about 300 mg, about 400 mg or about 500 mg. Smaller suppositories for pediatric use are also within the scope of the invention, which generally would be smaller and comprising in the range of 50-750 mg fatty acid active agent, such as in the range of 50-500, e.g. about 50 mg, about 75 mg, about 100 mg, about 200 mg, about 300 mg or about 400 mg. Depending on the desired dose and the desired total size of the suppository the amount of fatty acid active ingredient may comprise in the range of about 5 wt % to about 75 wt % of the total weight of the dosage form, such as in the range of about 5-50 wt %, including in the range of about 10-50 wt %, such as in the range of about 10-40 wt %.

A common size of molded or kneaded suppositories for adult use according to the invention is in the range of about 2-3 mL, such as about 2.0 mL, about 2.2 mL or about 2.5 mL. Depending on the excipient composition, this would generally correspond to a weight in the range of about 1.5 to about 3 g, accordingly, the suppositories according to the invention are suitably in said weight range, such as about 1.8 g, about 2.0 g, about 2.2 g or about 2.5 g.

A suitable size for pediatric suppositories would generally be about half the above size, such as in the range of 0.5-1.5 mL, e.g. about 0.5 mL, about 0.8 mL, about 1.0 mL, about 1.2 or about 1.5 mL.

It has been found useful to include in the suppository dosage form of the invention an excipient oil component such as a triacylglyceride oil (the term triacylglyceride oil indicating herein a natural, synthetic or mixed oil which comprises dominantly triglycerides, such as any of the above mentioned oils, but may also include some fraction of diacylglycerides and monoacylglycerides), to reduce discomfort during action of the medicament and bowel movements. Accordingly, the dosage form of the invention preferably comprises in the range of about 5-50 wt % triacylglyceride oil, including the range of about 5-35 wt % triacylglyceride oil, such as more preferably in the range of about 5-25 wt %, such as about 5 wt %, about 10 wt %, about 15 wt % or about 20 wt %. The base is in these embodiments composed accordingly in order to have a desired melting point of the overall composition of the dosage form. Preferably the triacylglyceride oil is a pharmaceutical gradeoil, such as fish oil derived Omega oil as mentioned above, or any other suitable well defined pharmaceutical acceptable oil.

It is useful to include anti-oxidants in the dosage forms of the invention, such as but not limited to butylated hydroxyanisole (BHA), butylated hydroxytoluene (BHT), ascorbic acid or a salt thereof, a sulfatide salt, citric acid, propyl gallate, alfa-tocopherol, and ascorbyl palmitate. Depending on the selected antioxidant compound, a suitable amount is e.g. in the range of about 0.05-0.5 wt %, such as in the range of 0.1-0.3 wt %. Further preservative agents may included in some embodiments, such as any of those of the group consisting of benzoic acid or derivatives thereof, including of $C_{1-6}$-alkyl-p-hydroxy-benzoic acids, such as methyl-p-hydroxy-benzoic acid, ethyl-p-hydroxy-benzoic acid, propyl-p-hydroxy-benzoic acid, butyl-p-hydroxy-benzoic acid, and mixtures thereof. In a particular interesting embodiment, the preservative is a mixture of methyl-p-hydroxy-benzoic acid and propyl-p-hydroxy-benzoic acid, in the proportion of from about 3:1 to about 5:1 by weight, preferably in the proportion of about 4:1 by weight.

The preservative or preservatives is/are preferably present in the formulation in such a concentration of about 0.05-0.2% by weight calculated on the formulation, that it does not to any substantial extent impair the activity of the lipid or lipids.

The suppository dosage form of the invention are preferably provided in isolating packaging to further inhibit air oxidation, such as alu-alu blister packaging, Duma containers or the like.

Enema formulations are generally liquid or semi-liquid formulations to be administered with suitable pharmaceutical grade enema rectal applicator. Preferred applicators are those that deliver the suitable dose of the formulation by breaking open a sealed dosage form container, such as e.g. described in U.S. Pat. No. 4,657,900.

In another aspect, the invention provides a method for stimulating and/or initiating the process of defecation, which comprises administering to the rectum and/or lower intestines one or more fatty acids. The method is based on the stimulating effect of the fatty acids on the polymodal nocireceptors in the rectal mucosa. The fatty acid is preferably selected from any of the above mentioned fatty acids and mixtures of fatty acids and can formulated in a suitable form such as in any of the forms described above.

As can be understood from the above discussion, free fatty acids are the preferred form of fatty acids in the method, although other forms are contemplated, such as fatty acid ethyl esters, salt of fatty acids and fatty acid monoglycerides.

The method will generally comprise administering in the range of about 100 to 2000 mg fatty acids, such as in the range of 100-1000 mg, or any of the above mentioned ranges and amounts.

In the presently preferred embodiment, the method comprises administration of the active ingredient to the rectum and/or lower intestines. Accordingly, the method preferably comprises administering dosage forms as described above, including suppositories, enemas or other formulation types introduced through the anus.

A further aspect of the invention provides fatty acid for use as a medicament for stimulating and inducing the process of defecation. The examples provided herein demonstrate a clear clinical effect of the fatty acids acting as active ingredient for the stated medical indication and clinical action. As illustrated in Example 6, the effect is attributed to fatty acids but not triacylglyceride oil used as excipient. The fatty acid of the invention is preferably in the form of free fatty acid or any of the other defined forms above and preferably the fatty acid is provided as a mixture of fatty acids. Suitably and practical mixtures can be obtained from natural sources, derived from animal or vegetative oils or mixture thereof, as those mentioned above.

In the below Example 1 is described how a preferred extract of free fatty acids is produced by acid hydrolysis of a marine fish oil. Accordingly, a fatty acid mixture obtainable from hydrolysis of natural oil, such as from a vegetable oil or fish oil, for use as a laxative medicament is included in the invention. The fatty acid of the invention is preferably formulated in a dosage form of the invention, such as in particular as a suppository, preferably as further described herein.

Fatty acids for use in the invention can be suitably provided by hydrolysis of natural oils such as those above mentioned. Hydrolysis of triglycerides can be acid or base catalysed. As illustrated in the accompanying Examples, acid hydrolysis of a natural oil such as fish oil yields useful fatty acids, the composition of the resultant fatty acid mixture is substantially similar to the fatty acid composition of the oil raw material and will vary depending on the natural source and any desired composition can be derived by mixing different sources, either mixing natural oils prior to hydrolysis or mixing individual fatty acids or fatty acid mixtures. The fatty acid composition of different fish species and fish oil is well documented and known to the skilled person.

Ethyl esters of fatty acids for use in the invention can be obtained by esterification of free fatty acids such as with a suitable lipase, such as but not limited to lipase from *Rhizomucor miehei* (MML), *Pseudomonas* sp. lipase (PSL) and *Pseudomonas fluorescens* lipase (PFL). See e.g. Halldorsson et al (2004), WO 95/24459, WO 00/49117 and U.S. Pat. No. 7,491,522.

Monoglycerides can be obtained by selective esterification with glycerol with lipase under suitable reaction conditions, for an overview see, Osman et al. (2006).

A further aspect of the invention provides pharmaceutical formulations and dosage forms with fatty acids and cyclodextrins. Cyclodextrins are cyclic oligosaccharides and are useful for forming host-guest complexes with hydrophonic molecules. The inventors have found that dry fatty acid powders can be readily provided in combination with cyclodextrins. Cyclodextrin compounds that are useful in the invention include alfa-cyclodextrin, beta-cyclodextrin and gamma-cyclodextrin and their derivatives, such as 2-hydroxypropyl-alfa-cyclodextrin, 2-hydroxypropyl-gamma-cyclodextrin and sulfobutylether gamma-cyclodextrin. Useful dry fatty acid powders can comprise about 1:1 ratio of fatty acids and cyclodextrins, or in the range of from 1:2 to 2:1 fatty acids to cyclodextrins, e.g. a ratio of about 2:1 (67:33) fatty acids: cyclodextrin, or a ration of about 3:2, or about 1:1, or about 2:3, or 2:1. Cyclodextrin-fatty acid compositions according to the invention were found to be substantially more stable than the fatty acids.

The dosage form is in some embodiments a dosage form for oral administration, such as a tablet, sachet or capsule. Such dosage forms can be formulated by conventional methods with the fatty acid-cyclodextrin complex converted to dry form as described herein.

Tablets are a preferred embodiment, they can be readily formulated by e.g. direct compression, dry granulation (slugging or roller compaction) or wet granulation. direct compression is preferred for this invention. Dry granulation consists of blending, slugging the ingredients, dry screening, lubrication, and compression. The wet granulation method is used to convert a powder mixture into granules having suitable flow and cohesive properties for tableting. The procedure includes mixing the dry ingredients in a suitable blender followed by adding a granulating solution under shear to the mixed powders to obtain a granulation. The damp mass is screened through a suitable screen and dried by tray drying or fluidized bed drying. Alternatively, the wet mass may be dried and passed through a mill. The overall process includes: weighing, dry powder blending, wet granulating, drying, milling, blending lubrication and compression. Direct compression is a relatively quick process where the powdered materials are compressed directly without changing the physical and chemical properties of the drug. The fatty acid compound, direct compression excipients and any other auxiliary substances, such as a glidant and lubricant are blended, e.g. in a twin shell blender or similar low shear apparatus before being compressed into tablets.

Excipients which may be present include one or more of diluents, binders, disintegrants, lubricants, glidants and colorants. A glidant may be added to improve the flow of powder blend in the hopper and into the tablet die. Lubricants are typically added to prevent the tableting materials from sticking to punches, minimize friction during tablet compression, and allow for removal of the compressed tablet from the die. Lubricants are commonly included in the final tablet mix in amounts usually less than 1% by weight. Lubricants which can be used in the invention include but are not limited to magnesium stearate, stearic acid, hydrogenated oil, and sodium stearyl fumarate.

Tablets of the invention can further comprise one or more diluent, added to increase the bulk weight of the blend resulting in a practical size for compression and/or affect the properties of the blend for compression. Typical diluents which can be used include for example dicalcium phosphate, calcium sulphate, lactose, dextrates, dextrins, cellulose (preferably microcrystalline cellulose), mannitol, sodium chloride, dry starch, pregelatinized starch and other sugars. Binders are used to impart cohesive qualities to the powdered material. Useful binders include starch, gelatin, sugars such as sucrose, glucose, fructose, mannitol, sorbitol, dextrose, and lactose, natural and synthetic gums, carboxymethylcellulose, methylcellulose, polyvinylpyrrolidone, ethylcellulose and waxes. A disintegrant may be incorporated to ensure that the tablet has an acceptable rate of disintegration. Typical disintegrants include starch derivatives, crospovidone, croscaramelose and salts of carboxymethylcellulose. Some binders, such as starch and cellulose, are also excellent disintegrants.

Another useful dosage form of the invention is a capsule. Suitable capsules of appropriate size for a given dosage size are well known to the skilled person and include but are not limited to hard gelatine capsules, soft gelatine and are more preferably hydroxypropyl methylcellulose capsules.

In the dosage form of the invention, the amount of active ingredient can be relatively large, such as in the range of about 50-2000 mg fatty acids, including the range of about 100-2000 mg, such as in the range of about 100-1000 mg, such as about 200-1000 mg, including about 200 mg, about 250 mg, about 300 mg, about 500 mg, about 750 mg or about 1000 mg. Consequently, it is preferred that the total amount of excipients in a tablet or capsule of the invention does not add too much mass to the dosage form. Accordingly, it is preferred that excipients comprise less than about 25 wt %, such as less than about 20 wt % and more preferably less than about 15 wt %.

Further useful embodiments include dosage forms for topical administration such as but not limited to an ointment, cream, lotion, gel, emulsion, liposomes, or paste. These dosage forms are suitably formulated with conventional ingredients and excipients. gels, such as for iontopophoresis, suspensions and emulsions, including oil/water (w/o), w/o, o/w/o, w/o/w emulsions or microemulsions. These dosage forms are suitably provided by mixing a dry powder of fatty acid-cyclodextrin complex with suitable ingredients, in a hydrophobic or hydrophilic basis. The basis may comprise hydrocarbons such as hard, soft or liquid paraffin, glycerol, waxes (e.g., beeswax, carnauba wax), metallic soap, a mucilage, an oil of natural origin such as corn, almond, castor, or olive oil, mineral oils, animal oils (perhydroxysqualene); or a fatty acid such as stearic or oleic together with an alcohol such as ethanol, isopropanol, and propylene glycol. The formulation may include any suitable surface active agent such as an anionic, cationic, or non-ionic surfactant such as sorbitan esters or polyoxyethylene derivatives thereof. Suspending agents such as natural gums, cellulose derivatives or inorganic materials such as silicaceous silicas may also be included. The formulations may additionally comprise absorption promoters, stabilizers, e.g. protein stabilizing agents, known in the art.

The topical dosage forms preferably include an antioxidant such as any of those mentioned above for oral dosage forms.

EXAMPLES

Example 1

Preparation of Fatty Acid Extract

Preparation of the fatty acid mixture from fish oil: The fatty acid mixture is extracted from fish oil (such as fish-liver oil, for example cod-liver oil) after hydrolysis in aqueous media. Sodium hydroxide (130 grams) is dissolved in a mixture of 1.0 liter of ethanol and 1.5 liter of purified water. Then 1000 grams of cod-liver oil is added and the mixture heated under reflux at 85° C. for 8 hours. Then after cooling to 5° C. 800 ml of 6M hydrochloric acid is added and the oil phase separated from the aqueous solution. The oil is then washed four times with 800 ml of purified water at 50° C. and finally dried at room temperature under vacuum. The fatty acid composition of the extract and the cod-liver oil used to prepare the extract is determined by gas-chromatography. The relative fatty acid composition of the extract is approximately the same as in the unhydrolyzed oil (Table 4).

TABLE 2

The fatty acid composition of triglycerides found in cod-liver oil and its fatty acid extract.

| | | Composition (%) | |
|---|---|---|---|
| Fatty acid | | Cod-liver | |
| Name | Number | oil | Fatty acid extract |
| Myristic acid | 14:0 | 3.4 | 3.8 |
| Palmitic acid | 16:0 | 10.2 | 11.4 |
| Palmitoleic acid | 16:1 n-7 | 6.6 | 7.0 |
| Stearic acid | 18:0 | 2.3 | 2.5 |
| cis-Vaccenic acid | 18:1 n-7 | 4.4 | 4.4 |
| Oleic acid | 18:1 n-9* | 17.6 | 18.8 |
| Linoleic acid | 18:2 n-6 | 1.2 | 1.3 |
| Moroctique acid | 18:4 n-3 | 2.1 | 2.1 |
| cis-11-Eicosenoic acid | 20:1 n-7 | 0.4 | 0.5 |
| Gondoic acid | 20:1 n-9 | 9.6 | 9.4 |
| Gadoleic acid | 20:1 n-11 | 1.9 | 2.1 |
| Eicosapentaenoic acid | 20:5 n-3 | 8.3 | 7.5 |
| Erucic acid | 22:1 n-9 | 0.6 | 0.6 |
| Cetoleic acid | 22:1 n-11 | 9.0 | 9.7 |
| Clupandonic acid | 22:5 n-3 | 1.4 | 1.4 |
| Docosahexaenoic acid | 22:6 n-3 | 11.1 | 9.7 |

*includes linolenic acid (18:3 n-3) that was not separated from 18:1 n-9 in the GC system. Cod-liver oil usually contains less than 1% linolenic acid.

Example 2

Suppositories with Fatty Acid Extract

Suppositories were prepared by the fusion method. White beeswax (Apifil Gattefossé, France; 50 grams), glycerol dibehenate (Compritol 888, Gattefossé; 19 grams) and hard fat (Suppocire NA 0, Gattefossé; 530 grams) were melted and mixed at about 75° C. and allowed to cool to 50° C. Then tocopherol antioxidant mixture (Coviox T70, Cognis, Germany; 1 gram), cod-liver oil (100 grams) and the fatty acid extract (300 grams) were added and after thorough mixing and cooling to 45° C. the mixture was poured into a suppository mold (2.2 ml) and cooled at room temperature. Suppositories containing 10% and 20% fatty acid extract, as well as suppositories containing either cod-liver oil (100 grams) or fatty acid extract (300 grams), where additional amounts of Suppocire NA 0 replaced the other ingredient, were prepared by the same method.

TABLE 3

| Ingredient | Amount in batch | Relative amount |
|---|---|---|
| Beeswax (Apifil) | 50 g | 5% |
| glycerol dibehenate (Compritol 888) | 19 g | 1.9% |
| hard fat (Suppocire NA 0) | 530 g | 53% |
| Tocopherol (Coviox T70) | 1 g | 0.1% |
| cod-liver oil | 100 g | 10% |
| fatty acid extract | 300 g | 30% |
| Total | 1000 g | |

Example 3

Ointment with Fatty Acid Extract

Ointments were prepared by the fusion method. Beeswax (Apifil, Gattefossé; 49 grams), glyceryl distearate (Precirol ATO, Gattefossé; 20 grams) and petrolatum (white soft paraffin Ph.Eur; 330 grams) were melted together over water bath at 65 to 75° C. After cooling to 50° C. cod-liver oil (300 grams), fatty acid extract (300 grams) and tocopherol antioxidant mixture (Coviox T70, Cognis; 1 gram) were added to this base. Then, after cooling to room temperature, the ointment was filled into 30 ml aluminum tubes.

Example 4

Double-Blind Study with Suppositories

A double-blind study was conducted with 30 healthy volunteers. On day 1 the participants underwent an anal examination and randomized into study group, receiving the active ingredients (suppositories and ointments containing 30% omega enriched fatty acid mixture, see Table 2 and Examples 2 and 3), and control group, receiving placebo (identical suppositories and ointments without fish-liver oil and the fatty acid mixture) for a total study period of two weeks. The study group consisted of 3 males and 12 females, with the mean age of 46 years. The control group consisted of 6 males and 9 females with the mean age of 43 years. The participants administered the suppositories in the rectum and applied the ointment to the perianal area twice a day with clinical examination after the first week with anal examination where any sign of erythema, inflammation, blood or sores were recorded. After the second week the volunteers underwent final examination. The participants also answered a questionnaire about the effect of the suppositories on their bowel movement during control examination after week one and two.

The anal examination conducted after week one and at the final control did not reveal any toxic skin reactions in either group. There was no statistically significant difference regarding complaints of itching or mild pain between the groups. In the study group 93% felt the urge for defecation and passed stools, most within 10 minutes after administration of suppositories. In the control group only 37% felt the urge for defecation after administration of suppositories. The difference was statistically significant (P=0,000). The suppositories clearly stimulated bowel movement causing defecation without causing diarrhea, mucosa secretion or any prolonged effect after defecation.

Example 5

Comparison—Suppositories with Fatty Acids Vs. TAG Oil

Five healthy volunteers participated in this study. On day one they administered rectally one suppository containing 10% omega enriched fish-liver oil and 30% omega enriched fatty acid mixture (see Table 2 and Example 2) and on day seven they administered identical suppository containing only the fish-liver oil (40%) but no free fatty acids. The suppositories containing the fish-liver oil and the fatty acid mixture stimulated bowel movement causing defecation in all participants while suppositories containing only the fish-liver oil did not.

Example 6

Tablets with Fatty Acid and Cyclodextrin

Dry powder containing free fatty acids were prepared by weighing 10 grams γ-cyclodextrin, 3 grams carboxymethylcellulose sodium (molecular weight 90,000 Da) and 0.02 grams benzalkonium chloride in a beaker glass and add pure water ad 90 ml. Then 9 grams of cod-liver oil and 1 gram of free fatty acid mixture (Example 1) was added to this solution. After thorough mixing the emulsion formed was lyophilized to form dry complex powder. Then 98.5 grams of the complex powder was mixed with 0.5 grams of silicon dioxide and 1 gram of magnesium stearate, and tablets (diameter 15 mm, weight 0.75 grams) prepared by direct compression.

Example 7

Dry Powder with Fatty Acids and Cyclodextrin

γ-cyclodextrin (gamma-cyclodextrin; 15 grams) was dissolved in 85 ml of water and 15 grams of the fatty acid mixture (Example 1) added to the solution (pH 7.4). After thorough mixing the emulsion formed was lyophilized to form dry complex powder.

Example 8

Virucidal Activity of Fatty Acid Extract and Fatty Acid-Cyclodextrin Complex

Monolayers of CV-1 cells (African green monkey kidney cell line) in 96-well cell culture plates (Nunc, Denmark) were use to determine virus infectivity titers. The cell culture medium was Eagle's minimum essential medium (MEM) with 10% fetal bovine serum (FBS) and the maintenance medium (MM) was MEM with 2% FBS. The fatty acid extract from cod-liver oil, fatty acid extract (Example 1) or fatty acid extract/γ-cyclodextrin complex (Example 7) was dissolved in MM to the desired concentration (0.5% and 1.0%) by vortexing for one min. The extract dilutions in MM were mixed with stock solution of herpes simplex virus type 1 (HSV-1) in ratio 4:1 and incubated at room temperature for 10 min. The viral infectivity in the mixtures was then immediately titrated by inoculation of 10-fold dilutions in MM into wells with CV-1 monolayers, 100 μL per well and four wells per dilution. The cell culture plates were incubated for 5 days at 37° C. and 5% $CO_2$ in air. Virus infectivity titers were then read and expressed as $\log_{10} CCID_{50}$ (50% cell culture infective dose) per 100 μL. The titers in mixtures with fatty acid extract were subtracted from the titer of the control mixture in which HSV-1 was diluted 4:1 in MM. The difference, i.e. reduction of titer, was used as a measure of antiviral activity (see Table 5).

TABLE 4

The antiviral activity.

| Compound | Virus titer $\log_{10}$ | Virucidal activity |
|---|---|---|
| Fatty acid extract in a γ-cyclodextrin complex | ≦1.5 | >5.0 |
| Cod-liver oil (undiluted) | 0 | 0 |
| Fatty acid extract (undiluted) | ≦1.5 | >5.0 |
| HSV-1 control | 6.57 ± 0.10 | X |

REFERENCES

J. J. Kabara, Fatty acids and derivatives as antimicrobial agents. In: The pharmacological effect of lipids. Edited by J. J. Kabara. The American Oil Chemists Society, St. Louis, Mo., 1978, pp. 1-13.

S. Khulushi, H. A. Ahmed, P. Patel, M. A. Mendall, T. C. Northfield, The effect of unsaturated fatty acids on *Helicobacter pylori* in vitro, J. Med. Microbiol., 42, 276-282, 1995.

N. M. Carballeira, New advances in fatty acids as antimalarial, antimycobacterial and antifungal agents, Prog. Lipid Res., 47, 50-61, 2008).

H. Thormar, H. Hilmarsson, The role of microbicidal lipids in host defense against pathogens and their potential as therapeutic agents, Chem. Phys. Lip., 150, 1-11, 2007.

C. Vieira, S. Evangelista, R. Crillo, A. Lippi, C. A. Maggi and S. Manzini, Effect of ricinoleic acid in acute and subcronic experimental models of inflammation, Med. Inflammation, 9, 223-228, 2000.

G. A. Burdock, I. G. Carabin and J. C. Griffiths, Toxicology and pharmacology of sodium ricinoleate, Food Chem. Tox., 44, 1689-1698, 2006.

B. E. Lacy and L. C. Levy, Lubiprostone: a novel treatment for chronic constipation, Clin. Interv. Aging, 3, 357-364, 2008.

Osman, F., Ashour A. E., Gad, A. M., Monoglycerides: I. Synthesis by Direct Esterification of Fatty Acids and Glycerol, Fette, Seifen, Anstrichmittel, 70, 331-333, 2006.

Halldorsson, B. Kristinsson and G. G. Haraldsson. Lipase selectivity toward fatty Acids Commonly Found in Fish Oil. *Eur. J. Lipid Sci. Tech.* 106, 79-87, 2004.

The invention claimed is:

1. A pharmaceutical dosage form in the form of a suppository for rectal administration for inducing defecation, said dosage form comprising as an active ingredient a mixture of fatty acids comprising at least about 20 wt % monounsaturated and polyunsaturated fatty acids of which at least about is 5 wt % polyunsaturated fatty acids, wherein the mixture of fatty acids is derived from marine organism material selected from the group consisting of marine animal oil derived from a source selected from fish liver oil including cod liver oil, tuna oil; fish flesh or fish meal including flesh or meal from herring, capelin, mackerel, menhaden, sardine, anchovy, horse mackerel, blue whiting, and tuna; planktonic organisms, squid and molluscs, and any mixture thereof.

2. The pharmaceutical dosage form of claim 1, wherein said mixture of fatty acids is in the form selected from free fatty acid, fatty acid ethyl ester and fatty acid monoglyceride.

3. The pharmaceutical dosage form of claim 1, wherein said mixture of fatty acids comprise one or more saturated or unsaturated fatty acid with a carbon chain length in the range of C4 to C36.

4. The pharmaceutical dosage form of claim 1, comprising in the range of 50-2000 mg fatty acids.

5. The pharmaceutical dosage form of claim 1, which comprises in the range of 10-50 wt % fatty acids and further comprises in the range of 5-25 wt % triacylglyceride oil.

6. The pharmaceutical dosage form of claim 1, further comprising cyclodextrin.

7. A method of stimulating and/or initiating the process of defecation comprising administering to the rectum one or more fatty acid in order to stimulate the polymodal nocireceptors in the rectal mucosa the dosage form of claim 1.

8. The method of claim 7, wherein said one or more fatty acids is in the form selected from free fatty acid, fatty acid ethyl ester and fatty acid monoglyceride.

9. The method of claim 7, comprising administering in the range of 50-2000 mg fatty acids.

10. The method of claim 7, wherein the one or more fatty acid is formulated in a suppository which further comprises in the range of about 5-25 wt % triacylglyceride oil.

* * * * *